(12) United States Patent
Gifford (10) Patent No.: US 6,242,222 B1
(45) Date of Patent: Jun. 5, 2001

(54) PROGRAMMED SEQUENTIAL MUTAGENESIS

(75) Inventor: David K. Gifford, Weston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/194,936

(22) PCT Filed: Jun. 6, 1997

(86) PCT No.: PCT/US97/09942

§ 371 Date: May 26, 1999

§ 102(e) Date: May 26, 1999

(87) PCT Pub. No.: WO97/46670

PCT Pub. Date: Dec. 11, 1997

Related U.S. Application Data (60) Provisional application No. 60/019,250, filed on Jun. 7, 1996.

(51) Int. Cl.⁷ .............................. C12Q 1/68; C12P 19/34; C07H 21/04
(52) U.S. Cl. ............................ 435/91.2; 435/6; 536/24.3; 536/24.33
(58) Field of Search ...................... 435/6, 91.2; 536/24.3, 536/24.33

(56) References Cited

U.S. PATENT DOCUMENTS

| | | | |
|---|---|---|---|
| 5,521,077 | 5/1996 | Khosla et al. | 435/172.3 |
| 5,804,373 | 9/1998 | Schweitzer et al. | 435/6 |

FOREIGN PATENT DOCUMENTS

| | | | |
|---|---|---|---|
| 0466083A2 | 7/1991 | (EP) | C12N/75/10 |
| WO 96/17056 | 6/1996 | (WO) | C12N/75/10 |

OTHER PUBLICATIONS

Shimada, PCR based site directed mutegenesis, Methods in Mol. Biol., vol.57: In vitro mutaganesis protocols chapter 14, pp. 157–165, M.K. Trower, Humana Press, Inc., Totowa, NJ, 1996.*

Michael, Mutagenesis by incorporation of a phosphorylated oligo during PCR amplification,412, BioTechniques, 1994.*

Breslauer et al. (1986), "Predicting DNA Duplex Stability From the Base Sequence," 83 *Proc. Natl. Acad. Sci. USA* 3746–3750.

Werntges et al. (1986), "Mismatches in DNA Double Strands: Thermodynamic Parameters and Their Correlation to Repair Efficiencies," 14 *Nucleic Acids Res.* 9:3773–3791.

Head (1987), "Formal Language Theory and DNA: An Analysis of the Generative Capacity of Specific Recombinant Behaviors," 49 *Bulletin of Math. Biol.* 6:737–759.

(List continued on next page.)

*Primary Examiner*—Kenneth R. Horlick
*Assistant Examiner*—Joyce Tung
(74) *Attorney, Agent, or Firm*—Testa, Hurwitz & Thibeault, LLP (57) ABSTRACT

Methods and products are provided for the oligonucleotide-mediated polymerase-dependent mutation of template nucleic acid sequences in a programmed sequence over multiple rounds of nucleic acid synthesis. The methods employ series of mutagenic primers, all of which may be present in the initial reaction system, in which at least some of the mutagenic primers do not bind to or promote polymerization from the original template nucleic acids, but do bind to and promote polymerization from the mutagenized products of earlier rounds of the program of sequential mutagenesis. The products of the invention include mixtures of such mutagenic primers. The products and methods have applications in the biological and computational sciences.

13 Claims, 5 Drawing Sheets

OTHER PUBLICATIONS

Ito et al. (1991), "A General Method for Introducing a Series of Mutations Into Cloned DNA Using the Polymerase Chain Reaction," 102 *Gene* 1:67–70.

Aiyar et al. (1993), "Modification of the Megaprimer Method of PCR Mutagenesis: Improved Amplification of the Final Product," 14 *BioTechniques* 3:366–368.

Barettino et al. (1993), "Improved Method for PCR–Mediated Site–Directed Mutagenesis," 22 *Nucleic Acids Res.* 3:541–542.

Berger et al. (1993), "Phoenix Mutagenesis: One–Step Reassembly of Multiply Cleaved Plasmids with Mixtures of Mutant and Wild–Type Fragments," 214 *Anal. Biochem.* 571–579.

Adleman (1994), "Molecular Computation of Solutions to Combinatorial Problems," 266 *Science* 1021–1024.

Dwivedi et al. (1994), "Generation of Multiple Mutations in the Same Sequence Via the Polymer Chain Reaction Using a Single Selection Primer," 221 *Analytical Biochem.* 2:425–428.

Gifford (1994), "On the Path to Computation with DNA," 266 *Science* 993–994.

Piechocki et al. (1994), "Oligonucleotide Design and Optimized Protocol for Site–Directed Mutagenesis," 16 *BioTechniques* 4:702–707.

Shayiq et al. (1994), "Multiple In Vitro Site–Directed Mutagenesis Using Asymmetric Polymerase Chain Reaction," 221 *Analytical Biochem.* 1:206–208.

Weiner et al. (1994), "Rapid PCR Site–Directed Mutagenesis," 4 *PCR Methods and Applications* S131–S136.

Baum (1995), "Building an Associative Memory Vastly Larger Than the Brain," 268*Science* 583–585.

Beaver (1995), "Molecular Computing," pp. 1–12; Penn State University, University Park, PA.

Boles et al. (1995), "A Rapid and Highly Efficient Method For PCR–Based Site–Directed Mutagenesis Using New Primer," 28 *Curr. Genet.* 2:197–198.

Liang et al. (1995), "An Efficient and Optimized PCR Method with High Fidelity for Site–Directed Mutagenesis," 4 *PCR Methods and Applications* 269–274.

Lipton (1995), "DNA Solution of Hard Computational Problems," 268 *Science* 542–545.

Smith et al. (1995), "DNA Computers In Vitro and Vivo," *NEC Technical Report* 1–23.

Guarnieri et al. (1996), "Making DNA Add," 273 *Science* 220–223.

Tu et al. (1996), "Generation of a Combination of Mutations by Use of Multiple Mutagenic Oligonucleotides," 20 *BioTechniques* 3:352–354.

Chatellier et al. (1997), "Combinatorial Scanning Site–Directed Mutagenesis," *Gene Cloning and Analysis: Current Innovations* Chapter 8, pp. 117–132, Horizon Scientific Press, Wymondham, U.K.

Hartemink et al. (1997), "Thermodynamic Simulationof Deoxyoligonucleotided Hybridization for DNA Computation," pp. 1–11.

Urban et al. (1997), "A Rapid and Efficient Method for Site–Directed Mutagenesis Using One–Step Overlap Extension PCR," 25 *Nucleic Acids Res.* 11:2227–2228.

* cited by examiner

FIG 1A Annealing Step

FIG 1B Polymerization and Ligation Step

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "Synthetic primer"

(iv) ANTI-SENSE: NO

(xi) SEQUENCE DESCRIPTION: SEQ ID NO: 1:

AACGGATTAC GC            12

(2) INFORMATION FOR SEQ ID NO: 2:

(i) SEQUENCE CHARACTERISTICS:
      (A) LENGTH: 12 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "Synthetic primer"

(iv) ANTI-SENSE: NO

(xi) SEQUENCE DESCRIPTION: SEQ ID NO: 2:

TTCCGATAAC GC            12

(2) INFORMATION FOR SEQ ID NO: 3:

-continued

```
    (i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iv) ANTI-SENSE: NO (xi) SEQUENCE DESCRIPTION: SEQ ID NO: 3:

TACCGATTAC GC                                                      12

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iv) ANTI-SENSE: YES (xi) SEQUENCE DESCRIPTION: SEQ ID NO: 4:

GCGTAATCCG TTGCGTTATC GGAA                                         24

(2) INFORMATION FOR SEQ ID NO: 5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iv) ANTI-SENSE: NO (xi) SEQUENCE DESCRIPTION: SEQ ID NO: 5:

AACGGATTAC GCTTCCGATA ACGC                                         24
```

PROGRAMMED SEQUENTIAL MUTAGENESIS

This application is a 371 of 97/09942, filed Jun. 6, 1997, which claims the benefit of provisional application 60/019, 250 filed Jun. 7, 1996.

GOVERNMENT SUPPORT

This invention was made with government support under Contract Number DABT63-95-C-002 awarded by the Department of the Army (Fort Huachuca). The government has certain rights in the invention.

FIELD OF THE INVENTION

The present invention is related to the fields of biochemistry, molecular biology and molecular genetics. In particular, the present invention is related to the controlled production of nucleic acids or nucleic acid analogs bearing predetermined alterations or mutations in their base sequences. The present invention has applications in fields including biochemistry, molecular biology and molecular genetics, as well as in the computational, pharmaceutical, and medical sciences.

BACKGROUND OF THE INVENTION

Oligonucleotide-mediated, site-directed mutagenesis was developed in the 1970's in bacteriophage φX174 (see, e.g., Weisbeek and Van de Pol); Hutchinson and Edgell (1971)) and in *E. coli* (see, e.g., Hutchinson et al. (1978); Razin et al. (1978)) as a means of introducing specific, predetermined changes or "mutations" at specific, predetermined sites in DNA molecules replicated in vivo. Subsequently, in vitro techniques for oligonucleotide-mediated mutagenesis have become routine in the fields of molecular genetics and biotechnology to introduce mutations into relatively long nucleic acid molecules (see, e.g., Sambrook et al. (1989)).

In brief, these techniques depend upon the facts that (1) under appropriate conditions, imperfectly complementary nucleic acids of sufficient length are capable of hybridizing to form heteroduplexes with mismatched or non-complementary base pairings, and (2) template-dependent polymerase-mediated nucleic acid synthesis proceeds 5'→3' from "primer" sequences duplexed to a template sequence. Therefore, to introduce a change or mutation into a relatively long sequence, a relatively short oligonucleotide may be prepared which includes the desired mutation and which will (1) hybridize to a complementary portion of the template sequence, and (2) serve as a mutagenic primer to support template-dependent polymerase-mediated synthesis of the relatively longer nucleic acid bearing the desired mutation. In practice it has been shown that single or multiple mutations may be introduced to nucleic acids of hundreds or thousands of nucleotides using template nucleic acids and one or more mutagenic oligonucleotide primers in vivo or in vitro.

In molecular biology and biotechnology, oligonucleotide-mediated mutagenesis can be used, inter alia, to introduce mutations in protein-encoding nucleic acids to introduce, remove or alter (1) one or a few amino acids in the encoded polypeptide products, (2) genetic regulatory sites (e.g., start or stop codons, promoter or enhancer sequences, polyadenylation sites, intron-exon splicing sites), and (3) restriction enzyme cleavage sites; as well as to create (4) large pools or libraries of combinatorially differing nucleic acid sequences which can be used to create corresponding pools or libraries of combinatorially differing polypeptides.

More recently, nucleic acids have been investigated for their potential utility in the computational sciences because, inter alia, their nucleotide sequences provide a molecular-scale medium for information storage, and because those sequences may be manipulated by the various means known and employed in the biological sciences (e.g., restriction, ligation, polymerase-dependent amplification and oligonucleotide-mediated mutagenesis). Notably, Adelman (1994, 1995) and others have used nucleic acid molecules to encode information and have used the reactions of large populations of nucleic acids in solution as massively parallel processors to find the solution to "Hamiltorian-path" problems.

Prior to the present invention, however, no method or products have been described for the introduction of mutations in a programmed sequential manner, in which one mutation causes base changes that enable later mutations. As described herein, such methods and products have utilities in both the biological and computational sciences.

SUMMARY OF THE INVENTION

The present invention is directed to methods of performing programmed sequential mutagenesis on template nucleic acids or nucleic acid analogs. In the methods, an original template nucleic acid or nucleic acid analog is provided which bears at least one target sequence. Also provided are at least two species of mutagenic primers which may be nucleic acids or nucleic acid analogs. The first mutagenic primers include a first target-binding sequence which is capable of hybridizing to a target sequence of the original template under conditions permissive for polymerase mediated nucleic acid synthesis, and which is non-complementary to that target sequence at one or more nucleotide or nucleotide analog positions. The second mutagenic primers include a second target-binding sequence capable of hybridizing to a second target sequence which is not present in the original template sequence but which is present in the mutagenic products of polymerization from the first mutagenic primers. The second mutagenic primers also include at least one nucleotide or nucleotide analog which is non-complementary to the second target sequence. Therefore, when the template and first mutagenic primers are subjected to a first round of nucleic acid synthesis, the first mutagenic primers bind to and promote polymerization from the template to produce a first set of mutagenized products. In a second round of nucleic acid synthesis, the second mutagenic primers, which could not bind to and promote polymerization from the original template sequence, are capable of binding to and promoting synthesis from a target sequence mutagenized by the first mutagenic primers. Thus, the mutagenesis of the original sequence proceeds in a programmed, sequential manner and the mutagenic product profile also changes from round to round in a programmed sequential manner.

The methods of the invention may be performed with more than two sets of mutagenic primers and may include more than two rounds of nucleic acid synthesis. Conveniently, the methods may be employed with thermally cycled nucleic acid polymerization methods, and the various sets of mutagenic primers may be added to the reaction mixture prior to the rounds in which they are intended to be effective. Thus, a program of mutagenesis may be designed with N rounds of mutagenesis employing N or more sets of mutagenic primers in a single reaction mixture. Alternatively, the methods may be performed with other techniques of oligonucleotide-mediated mutagenesis, such as those employing phage or bacteria.

The methods may also be employed using outer primers which do not introduce mutations to the template sequences, but which allow for the production of longer mutagenized products when the products of polymerization from the outer and mutagenic primers are ligated in vivo or in vitro. The outer primers may be either 5' or 3' or outer primers.

Preferably, the target sequences for the mutagenic and outer primers are sequences of at least 10, 15 or 20 nucleotides or nucleotide analogs. In addition, if the mutagenic primers are at least 10 nucleotide or nucleotide analogs in length, the mutagenic primers may preferably include 1–4 nucleotide or nucleotide analogs which are non-complementary to their corresponding target sequence bases. If the mutagenic primers are at least 15 nucleotide or nucleotide analogs in length, the mutagenic primers may preferably include 1–7 nucleotide or nucleotide analogs which are non-complementary to their corresponding target sequence bases.

Many variations on the methods of the invention are described. Such variations include the inclusion in a reaction mixture of multiple original templates) the use of stop primers, the design of a sequential mutagenesis program in which products of one round of synthesis may serve as primers in a subsequent round, the use of multiple primers per target sequence, the use of limiting primers, and the inclusion in a reaction mixture of various protein elements which facilitate the polymerization reaction or which alter the resulting products.

In another aspect, the present invention provides for reagents for use in programmed sequential mutagenesis. These reagents comprise mixtures of mutagenic primers for the above-described methods and, therefore, comprise mixtures of (1) a first set of one or more mutagenic primers which will bind to one or more target sequences within a template sequence under at least one set of conditions permissive for polymerase-mediated nucleic acid synthesis to create a first set of one or more mutagenized products, and (2) a second set of one or more mutagenic primers which will not bind to any target sequence within the original template sequence under those conditions, but which will bind to target sequences in the mutagenized products of the first set of mutagenic primers, under substantially similar conditions permissive for polymerase-mediated nucleic acid synthesis to create a second set of one or more mutagenized products.

The methods and products of the invention have particular utility in the fields of molecular biology or biotechnology, and in computational science. In particular, the methods may be employed to conduct programmed sequential mutagenesis of nucleic acids which encode polypeptide sequence and, thereby, produce mutagenic products which encode pools or libraries of combinatorially mutated polypeptides. The methods may also be employed to produce nucleic acid-based computational machines including unary counters and string re-writing rules.

DETAILED DESCRIPTION OF THE INVENTION

The present invention depends, in large part, upon the selection and use in site-directed mutagenesis techniques of novel sets of mutagenic primers which direct or "program" the introduction of mutations into a "template" nucleic acid in a predetermined temporal sequence and in predetermined physical combinations. That is, the present invention is distinguished, in part, by the use of sets of mutagenic primers in site-directed mutagenesis which are related to each other and to the original template sequence such that (a) the original template sequence is mutated in a predetermined temporal sequence of steps or "rounds" of mutagenesis, each round producing characteristic sets of mutagenized products which differ from the characteristic sets of products of prior rounds, and (b) at least some of the mutagenic primers are substantially incapable of directing mutagenesis of the original template nucleic acid but are specifically designed to be capable of directing the further mutagenesis of a product of an earlier round of mutagenesis. Thus, the present invention employs at least some mutagenic primers which will bind to previously mutated target sequences but not to their "ancestral" sequences in the original template and, therefore, the process of mutagenesis can be carried out in rounds with a predetermined or programmed sequence of mutations occurring in each round.

Definitions

In order to more clearly and concisely describe the subject matter of the present invention, and to aid in the exposition of the subject matter disclosed herein, the following definitions are provided for certain terms used in the following disclosure and appended claims.

Original template. As used herein, the term "original template" means the nucleotide sequence of the original nucleic acid (or nucleic acid analog) which is subjected to the mutagenic methods of the present invention. That is, the original template is the nucleotide sequence of the original nucleic acid (or nucleic acid analog) which is the subject of the first "round" of mutagenesis in accordance with the methods of the present invention. The original template may be a "sense" or "antisense" nucleic acid, a naturally occurring or synthetically produced nucleic acid, a wild-type or mutant sequence (including sequences previously subjected to site-directed mutagenesis apart from the methods of the present invention), or a nucleic acid analog (e.g., phosphorothioate-linked oligonucleotides or peptide-linked nucleic acids) of any of the foregoing.

Round. As used herein, the terms "round" of nucleic acid synthesis, or "round" of mutagenesis, refer to the nucleotide template-dependent, enzymatic process by which a single-stranded nucleic acid is produced which is substantially complementary, with or without the incorporation of mutations, to a template nucleic acid (or nucleic acid analog) molecule. During such a "round," complementary nucleic acids are produced by a polymerase and, with or without the aid of a ligase, and with or without the incorporation of a mutagenic primer, a nucleic acid molecule substantially complementary to the template is produced. A "round" of synthesis or mutagenesis must be distinguished from a thermal "cycle" in a polymerase chain reaction (PCR) process: As disclosed herein, a single PCR thermal cycle may include more than one "round" of nucleic acid synthesis or mutagenesis.

Target sequence. As used herein, a target sequence is a nucleotide sequence to which a mutagenic primer binds with imperfect complementarity such that, after a round of nucleic synthesis (polymerization and ligation), a mutagenized nucleic acid product is produced which incorporates the mutagenic primer and, therefore, bears a mutation relative to the target sequence. Each target sequence is a subset of a template sequence or the complement of a template sequence. Significantly, the target sequence need not be a subset of the original template sequence but, rather, may be a subset of a mutagenized nucleic acid product derived from the original template. Typically, target sequences will comprise at least 10, more preferably 15, and most preferably over 20 oligonucleotides (or oligonucleotide analogs).

Mutagenic primer. As used herein, the term "mutagenic primer" refers to a nucleic acid (or nucleic acid analog) comprising a target-binding nucleotide sequence which is substantially, but not completely, complementary to a nucleotide sequence of a target nucleic acid (or nucleic acid analog) sequence. The target nucleic acids for a mutagenic primer of the present invention may be included not only in the original template sequence but, significantly, the mutagenized product sequences which may result from incorporation of other mutagenic primers into the original template. As a general matter, the mutagenic primers of the present invention will comprise at least 10, more preferably 15, and most preferably over 20 oligonucleotides (or oligonucleotide analogs). For relatively short primers (e.g., 10–15 base pairs), the number of non-complementary or mismatch bases between the primer and target is preferably limited to 1–4 but may be as high as 7. For longer primers, as will be obvious to one of ordinary skill in the art, a greater number of mismatches may be included while still resulting in the desired hybridization of the primer and target, and the consequent incorporation of the target into a "mutagenized" nucleic acid product. As a general matter, a mutagenic primer has sufficient complementarity and length to hybridize to a target sequence under conditions permissive for polymerase-mediated nucleic acid synthesis and, optionally, ligase-mediated ligation of adjacent, duplexed nucleic acids. The selection of appropriate lengths for mutagenic primers for oligonucleotide-directed mutagenesis, as well as methods for their chemical synthesis, are well known in the art (see, e.g., Chapter 15 of Sambrook et al. (1989) *Molecular Cloning: A Laboratory Manual,* 2nd Edition, Cold Spring Harbor Laboratory Press, Cold Spring Harbor, N.Y.; Piechocki and Hines (1994) *BioTechniques* 16(4): 702–707).

Outer primer. As used herein, the term "outer primer" means a primer for polymerase-mediated nucleic acid synthesis which is essentially complementary to and selectively binds to region of a nucleic acid (or nucleic acid analog) template which is 5' or 3' of a target site. An outer primer is, therefore, a classical polymerase primer which may be used for priming polymerase-mediated template-dependent synthesis of a nucleic acid and which forms one end of the newly synthesized strand of complementary nucleic acid. Outer primers are distinguished from mutagenic primers in that they need not include mismatches and, typically, selectively bind to a 5' or 3' "outer" or "flanking" segment of the template. Outer primers may bind either 5' or 3' or to mutagenic primers (although only 5' outer primers are shown in the figures and examples for simplicity).

Mutagenized product. As used herein, a "mutagenized product" means a nucleic acid or nucleic acid analog product which results from binding of a mutagenic primer to an imperfectly complementary nucleic acid template, and nucleic acid synthesis from that primer, optionally with ligation to adjacent polymerase products. Thus, a mutagenized product will differ from the complement of its template at one or more nucleotide or nucleotide analog positions included within the mutagenic primer sequence which gave rise to the mutagenized product. The term "mutagenized product" also specifically includes nucleic acids, either identical or complementary in sequence, which are produced by template-dependent nucleic acid synthesis from a reference mutagenized product. Therefore, the term "mutagenized product" refers to both the original mutagenized products produced by a polymerase-mediated synthesis from a reference mutagenic primer, and to the sequences arising therefrom, either identical or complementary in sequence, by further rounds of nucleic acid synthesis. The term "mutagenized product" therefore includes an original mutagenized product and its "direct" descendants. A mutagenized product in one round of synthesis may serve as a template or primer in subsequent rounds.

Polymerase. As used herein, the term "polymerase" means a DNA or RNA polymerase, or a modified DNA or RNA polymerase, which is capable of directing template-dependent nucleic acid synthesis to yield nucleic acids which are substantially complementary to the template nucleic acid or nucleic acid analog, and which serve as templates for further rounds of nucleic acid synthesis. Preferred polymerases are those with low error rates (i.e., low rates of incorporation of non-complementary nucleotides), those that do not strand displace, those that do not have 5'→3' exonuclease activity, and those which are thermally stable. Preferred polymerases are DNA-dependent DNA polymerases, and thermally stable polymerases such as Vent.

Permissive conditions. As used herein, "conditions permissive for polymerase-mediated nucleic acid synthesis" means conditions of temperature, osmolality and the like which permit the hybridization of a given primer sequence, whether a mutagenic primer or an outer primer, to a target sequence, whether included within an original template or mutagenized product template, such that a template-dependent polymerase may catalyze the 5'→3' synthesis of a nucleic acid sequence perfectly or substantially complementary to the template sequence. As is well known in the art, permissive conditions may be determined experimentally by varying factors such as temperature and salt concentrations, and a substantial literature exists on the subject (see, e.g., Sambrook et al. (1989), and references therein). In addition, a substantial scientific literature has developed based upon theoretical (or thermodynamic), as well as hybrid experimental-theoretical considerations (see, e.g., Piechocki and Hines (1994); Werntges et al. (1986); Breslauer et al. (1986); and references cited therein). As used herein, a primer sequence is substantially incapable of initiating, promoting or supporting polymerase-dependent nucleic acid synthesis if the efficiency of the polymerization reaction from that primer (measured, for example, by moles of product per mole of primer) is an order of magnitude or, more preferably, 2–3 orders of magnitude lower than that of other primers present in the same reaction mixture. Similarly, as used herein, a primer is substantially incapable of hybridizing to a target sequence if the efficiency of hybridization of that primer (measured, for example, by association constants) is an order of magnitude or, more preferably, 2–3 orders of magnitude lower than that of other primers present in the same reaction mixture.

I. Programmed Site-Directed Mutagenesis

A. General

The present invention employs a modification of the standard methods of site-directed mutagenesis in combination with specially designed and selected mutagenic primers to provide a method of programmed sequential mutagenesis. The present methods may be employed with any of the art-known methods of oligonucleotide-mediated, site-directed mutagenesis but, preferably, is employed with oligonucleotide-mediated mutagenesis in conjunction with thermally cycled synthesis of nucleic acids. In the description which follows, therefore, the present invention will be described with respect to embodiments employing multiple cycles of nucleic acid polymerization based upon thermal cycling techniques. As will be appreciated by one of ordinary skill in the art, however, older techniques of nucleic acid amplification and oligonucleotide-mediated mutagenesis may be employed (e.g., bacteriophage $\phi$X174, see Hutchison and Edgell (1971); bacteriophage M13, see Sambrook et al. (1989)).

Figure 1A:
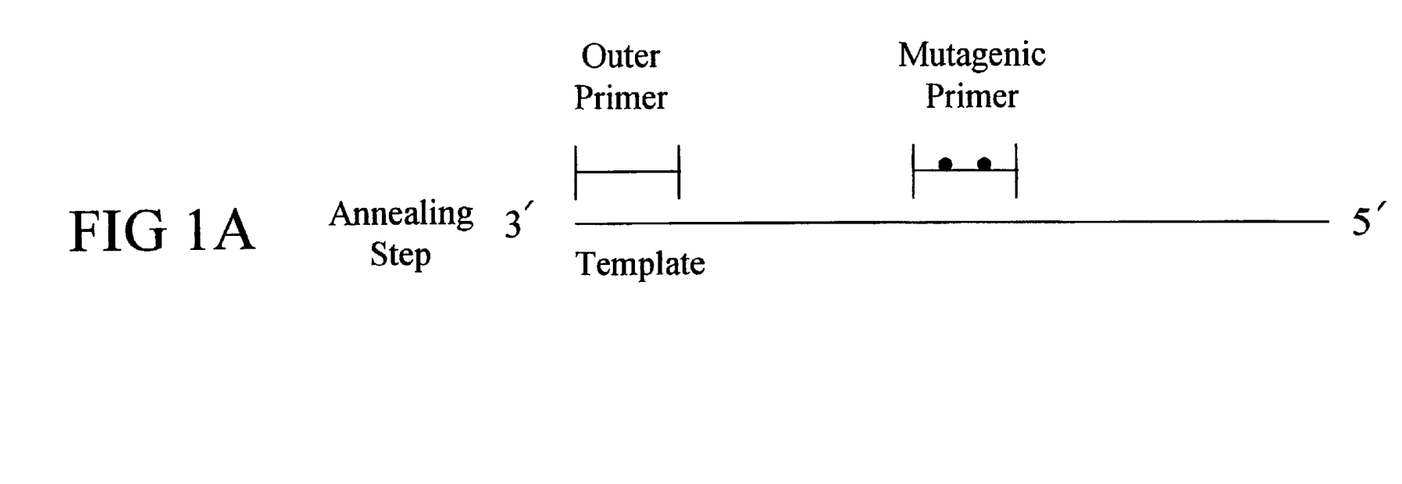
FIG. 1. This figure is a schematic representation of a "round" of site-directed mutagenesis.
Figure 1B:
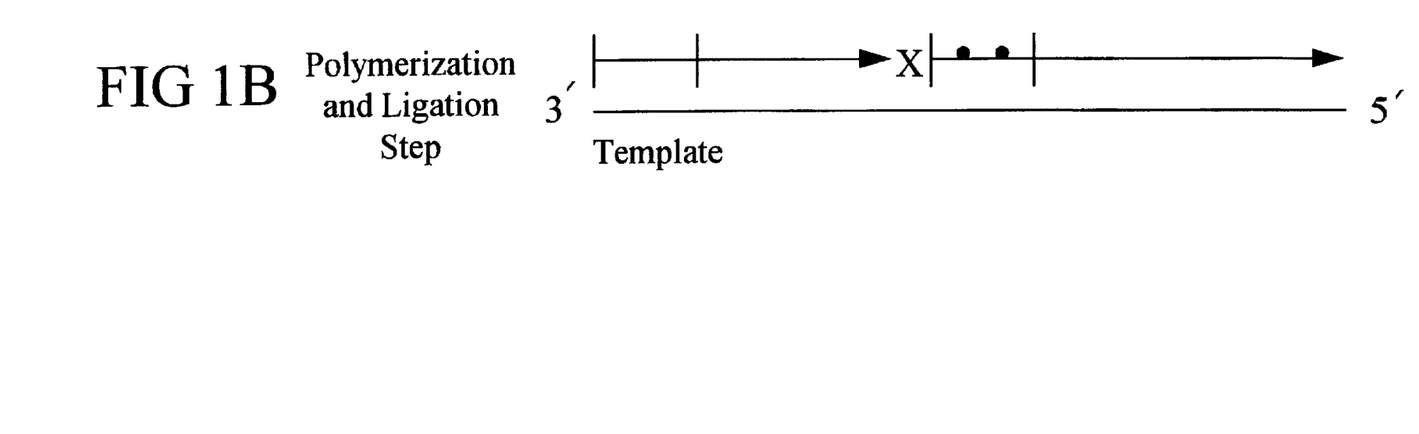

FIG. 1 provides a schematic representation of the process of site-directed mutagenesis. In FIG. 1(a), the mutagenic and outer primers anneal to the single-stranded template molecule, and in FIG. 1(b) the primers are extended by a polymerase reaction and then the product of the outer primer is ligated to the 5' end of the mutagenic primer. The "X" in FIG. 1(b) indicates the ligation event. This sequence of events corresponds to a "round" of mutagenesis.

Figure 2A:
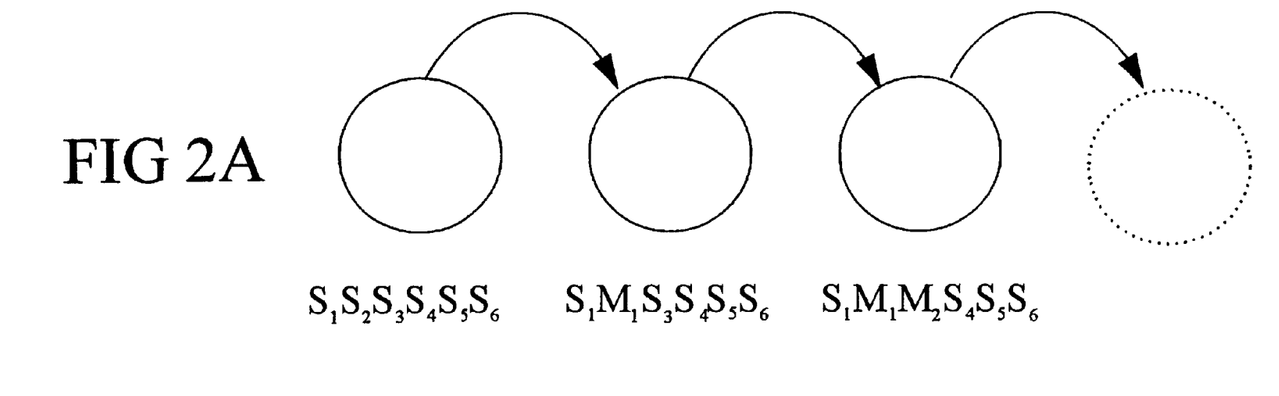
FIG. 2. This figure is a schematic representation of the process of programmed sequential mutagenesis.
Figure 2B:
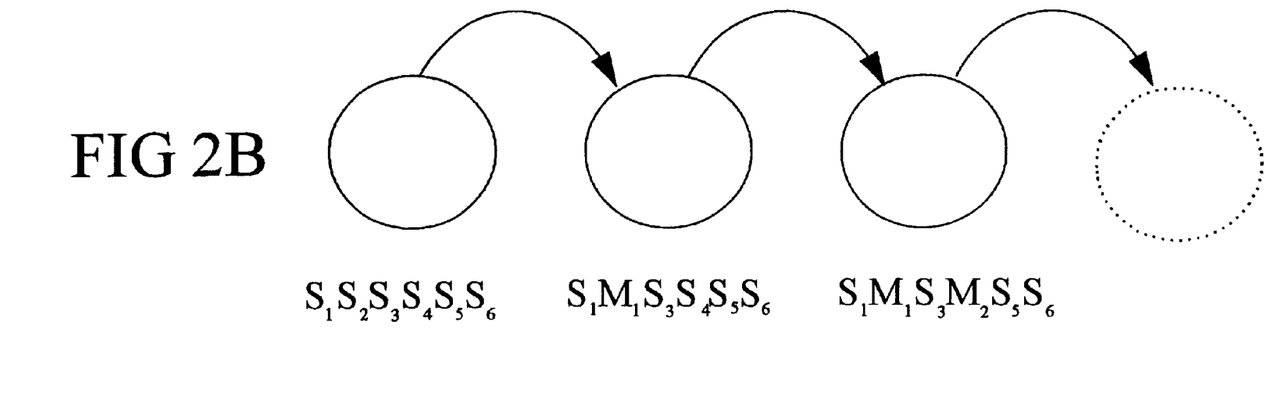

In the present invention, several rounds of mutagenesis are performed in which the mutagenic primers are selected such that the mutagenesis is programmed and sequential. FIG. 2 illustrates this concept. In this figure, each of the symbols "$S_1$" through "$S_6$" represents an oligonucleotide sequence of the original template sequence which may serve as a target for a mutagenic primer. The symbols "$M_1$" and "$M_2$" indicate mutagenized sequences. In FIG. 2(a), there is an original template sequence comprising sequences $S_1$ through $S_6$. In the first round of mutagenesis, the sequence $S_2$ is the target sequence and is mutagenized to sequence $M_1$. In the second round of mutagenesis, the adjacent sequence $S_3$ is the target sequence and is mutagenized to sequence $M_2$. Note that, in accordance with the present invention, the second mutagenic primer is selected such that the $S_2 \rightarrow M_1$ conversion in 2(a) must precede the $S_3 \rightarrow M_2$ conversion shown in the next round. That is, the primer should be substantially incapable of binding to the original (unmutated) template but be capable of directing mutagenesis of the first round mutagenized product. Thus, the first mutation is substantially a condition precedent for the binding of the mutagenic primer and the mutations follow a programmed sequence. In FIG. 2(b), a variation on this scheme is presented in which sequence $S_2$ is again mutagenized to $M_1$ in the first round. In the second round, the non-adjacent sequence $S_4$ is the target sequence and is mutagenized to sequence $M_2$. Again, by proper selection of the second mutagenic primer, the $S_2 \rightarrow M_1$ mutation is substantially a condition precedent to the $S_4 \rightarrow M_2$ mutation and, therefore, the mutations are programmed and sequential. As will be apparent to one of ordinary skill in the art, the second round mutagenized products may serve as templates for additional mutagenic primers and additional rounds of programmed sequential mutagenesis introducing additional mutations $M_i$ in varying patterns. In addition, variations are possible in which more than one mutagenic primer may bind to a template in any given round, resulting in the formation of mixtures of mutagenized products. These mixtures may be subjected to further rounds of programmed sequential mutagenesis, including the formation of more complex mixtures. In addition, more than one mutagenic primer may bind to a given template, permitting mutagenesis to occur at multiple loci on a given template. Alternatively, or in addition, more than one mutagenic primer may bind to a given target sequence within a template, introducing stochasticity in the product profiles due to competition between primers for binding sites.

As noted above, the present invention may be used with any form of oligonucleotide-mediated site-directed mutagenesis, but is particularly useful in combination with in vitro techniques employing thermally cycled polymerization reactions. Because the sequential mutagenesis is "programmed" by the mutagenic primers, it is possible to place all of the necessary primers and templates in a single reaction vessel at the start of the procedure because the "later round" primers will be inactive until their target sequences have been produced, but will survive in the reaction mixture until needed. (Naturally, additional primers may be added at various points if so desired.) In addition, because later round mutagenic primers may be dependent upon the successful introduction of earlier round mutations, primers may be designed such that there is no need to separate mutagenic primers between steps of the sequential mutagenesis. (Naturally, such separations may be performed at various points if so desired.) Thus, the present methods of programmed sequential mutagenesis provide for the sequential mutagenesis of nucleic acids in a single reaction vessel without the need for separations between mutagenic rounds.

B. A Simple Mutational Scheme: A Unary Counter

FIG. 3 illustrates a simple example of programmed sequential mutagenesis in accordance with the present invention. The symbols "A," "B" and "S" represent sequences of from 10–50 nucleotides and the symbols $\overline{A}$, $\overline{B}$ and $\overline{S}$ represent their complementary sequences. The several "S" sequences need not be identical to each other although, in some embodiments described below, they may be. The sequences may be designed or selected such that the total number of mismatches between sequences A and B are greater than (e.g., two-fold) the number of mismatches between A and any S or between B and any S. Sequences flanking the ASSSSS stretch on the original template may be assumed to be substantially non-complementary to any of the A, B or S sequences.

Figure 3A:
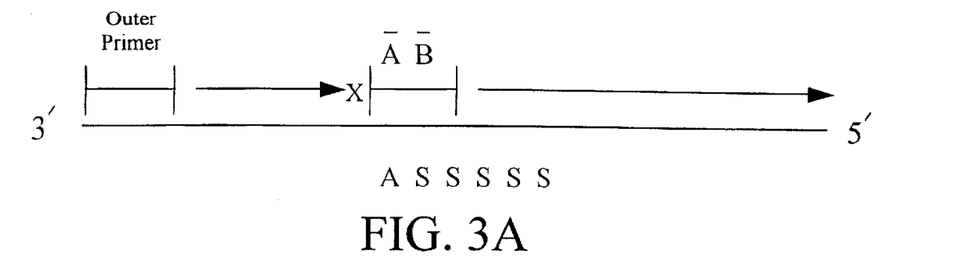
FIG. 3. This figures is a schematic representation of one example of programmed sequential mutagenesis showing the primers employed and nucleic acid polymerization and ligation at each step.

In FIG. 3(a), the first round of mutagenesis is shown. Annealing conditions are chosen such that mutagenic primer $\overline{A}$-$\overline{B}$ can bind at the A-S sequence of the template but not at any of the S-S sequences. This pairing is favored because it entails the fewest mismatches. The "antisense" outer primer also binds. Synthesis then proceeds from the 3' end of the outer primer to the 5' end of the mutagenic primer, and from the 3' end of the mutagenic primer to the end of the template. A ligase then joins these two partial sequences, as indicated by an "x," to form the first round mutagenized product which now contains the sequence $\overline{ABSSSS}$ rather than $\overline{ASSSSS}$.

Figure 3B:
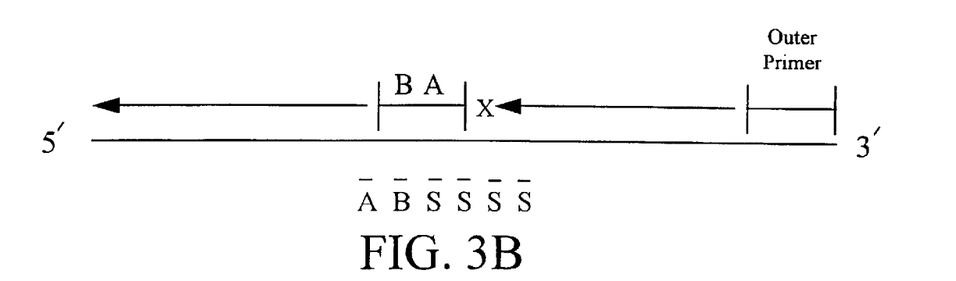

In the next round of mutagenesis, shown in FIG. 3(b), annealing conditions are chosen such that the mutagenic B-A primer can bind to the $\overline{B}$-$\overline{S}$ sequence but not to the $\overline{A}$-$\overline{B}$ or $\overline{S}$-$\overline{S}$ sequences. This pairing is favored because it entails the fewest mismatches. Note that this primer would not have found a partner with which to bind in the first round of mutagenesis. The "sense" outer primer also binds. Nucleic acid synthesis then proceeds from the 3' end of the outer primer to the 5' end of the mutagenic primer, and from the 3' end of the mutagenic primer to the end of the template. A ligase then joins these two partial sequences, as indicated by an "x," to form the second round mutagenized product which now contains the sequence ABASSS rather than ASSSSS.

Figure 3C:
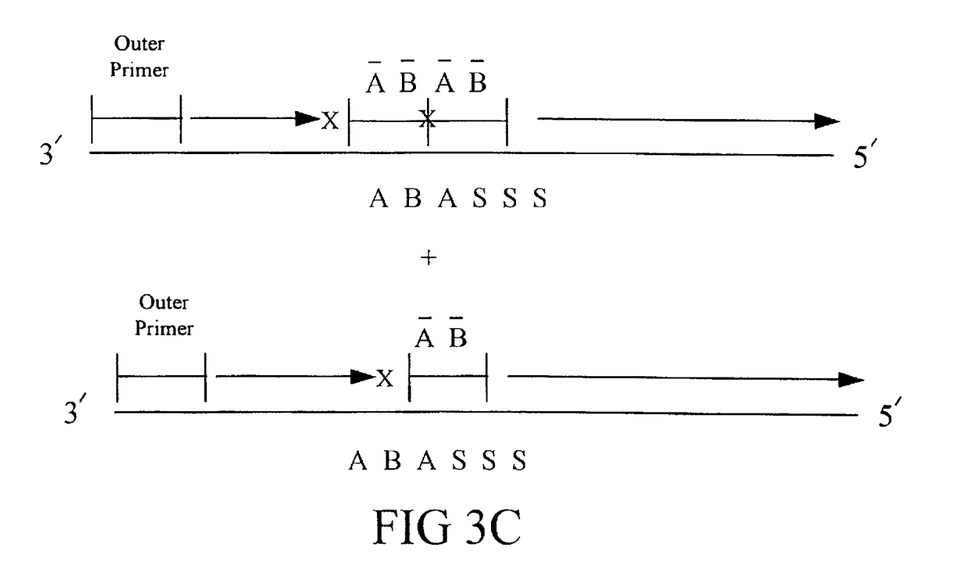

In the third round, as illustrated in FIG. 3(c), the $\overline{\text{A-B}}$ primer may bind to the second round mutagenized product in either of two positions. The favored site is the directly complementary A-B sequence which was produced by the first round of mutagenesis. If, however, the annealing conditions are the same as those employed in the first round, and if the $\overline{\text{A-B}}$ primer is present in sufficient molar excess, the $\overline{\text{A-B}}$ primer may bind not only to the perfectly complementary A-B sequence but also to the substantially complementary A-S sequence (as in round one). This is shown in FIG. 3(c). After synthesis and ligation, this round of mutagenesis will produce nucleic acids with the sequence ABABSS rather than the original ASSSSS.

The foregoing example is of interest in two respects: (a) It demonstrates the principle of programmed sequential mutagenesis by showing that certain sites will not be mutated in early rounds of mutagenesis but will be mutated in a predetermined temporal sequence only after the introduction of mutations at other sites, and (b) it demonstrates the development of a "unary counter" in which one additional site is mutated in each round of mutagenesis and, therefore, the number of mutations may be used as an indication of the number of rounds of mutagenesis or, conversely, induction of mutagenesis may be used as a means of "counting."

Naturally, the first and second mutagenic primers may be selected to operate on the same or opposite strands, and intervening rounds of nucleic acid synthesis, which do not mutagenize the products, may be employed to amplify all or some products.

C. More Complicated Mutational Schemes

As will be apparent to one of ordinary skill in the art from the foregoing description, a limitless number of variations on the process of FIG. 3 are possible which can produce a limitless number of predetermined programmed mutational variants. FIG. 4 illustrates an additional level of complexity. The symbols "A," "B," "C," "D," and "S" represent sequences of from 10–50 nucleotides and the symbols $\overline{\text{A}}$, $\overline{\text{B}}$, $\overline{\text{C}}$, $\overline{\text{D}}$ and $\overline{\text{S}}$ represent their complementary sequences. The several "S" sequences need not be identical to each other although, in some embodiments described below, they may be. The sequences may be designed or selected such that the total number of mismatches between sequences any of the pair-wise combinations of A, B, C, and D is greater than (e.g., two-fold) the number of mismatches between A and any S, between B and any S, between C and any S, or between D and any S. Sequences flanking the ASSSSS stretch on the original template may be assumed to be substantially non-complementary to any of the A, B, C, D or S sequences.

Figure 4A:
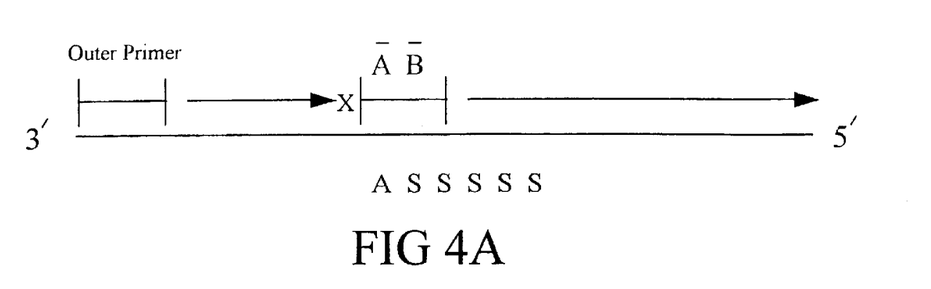
FIG. 4. This figures is a schematic representation of one example of programmed sequential mutagenesis showing the primers employed and nucleic acid polymerization and ligation at each step.

In FIG. 4(a), the first round of mutagenesis is shown. Annealing conditions are chosen such that mutagenic primer $\overline{\text{A-B}}$ can bind at the A-S sequence of the template but not at any of the S—S sequences. This pairing is favored because it entails the fewest mismatches. The "antisense" outer primer also binds. Nucleic acid synthesis then proceeds from the 3' end of the outer primer to the 5' end of the mutagenic primer, and from the 3' end of the mutagenic primer to the end of the template. A ligase then joins these two partial sequences, as indicated by an "x," to form the first round mutagenized product which now contains the sequence $\overline{\text{ABSSSS}}$ rather than $\overline{\text{ASSSSS}}$.

Figure 4B:
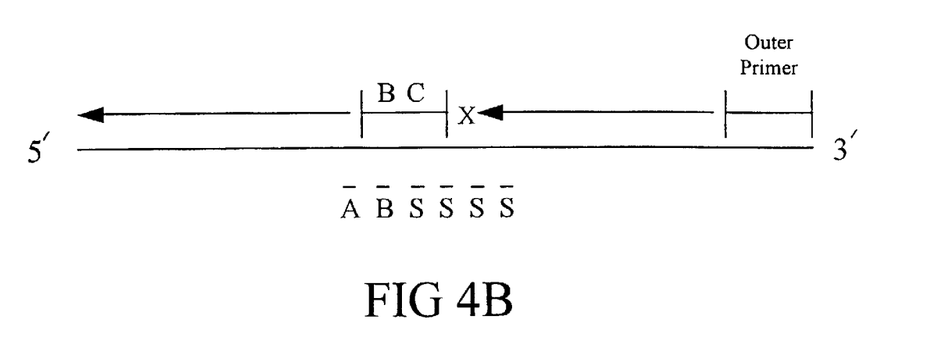

In the next round of mutagenesis, shown in FIG. 4(b), annealing conditions are chosen such that the mutagenic B-C primer can bind to the $\overline{\text{B-S}}$ sequence but not to the $\overline{\text{A-B}}$ or $\overline{\text{S—S}}$ sequences. This pairing is favored because it entails the fewest mismatches. Note that this primer would not have found a partner with which to bind in the first round of mutagenesis. The "sense" outer primer also binds. Nucleic acid synthesis then proceeds from the 3' end of the outer primer to the 5' end of the mutagenic primer, and from the 3' end of the mutagenic primer to the end of the template. A ligase then joins these two partial sequences, as indicated by an "x," to form the second round mutagenized product which will contain the sequence ABCSSS rather than ASSSSS.

Figure 4C:
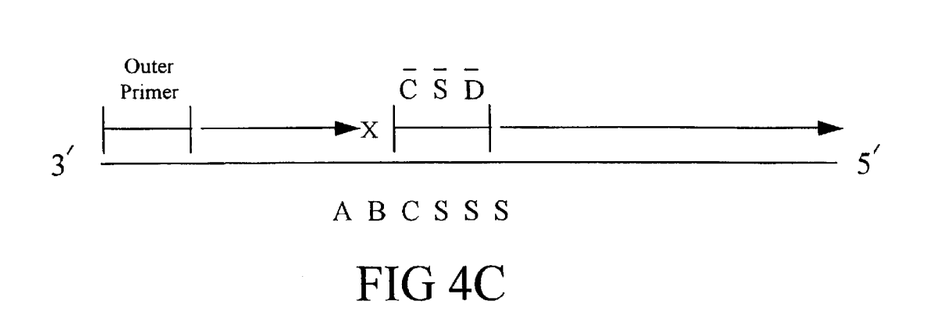

In the third round, as illustrated in FIG. 4(c), the primer $\overline{\text{C-S-D}}$ may bind to the second round mutagenized product in only one position. Note that this primer would not have been capable of binding to the original template or to the first round mutagenized product. After synthesis and ligation, this round of mutagenesis will produce nucleic acids with the sequence ABCSDS rather than the original ASSSSS.

D. Higher Levels of Complexity

Many additional layers of complexity may be added to the basic concept of programmed sequential mutagenesis as described herein. Briefly, these include at least the following.

(1) Multiple Original Templates. The methods of the present invention may be practiced upon starting mixtures which include multiple original templates. These original templates may then be mutagenized simultaneously in the same reaction vessel using sets of mixtures of primers which may include primers which are specific to only one template (or one of its mutagenized products) or which may serve to mutagenize both templates (or mutagenized products of both templates). Such reactions involving mixtures of original templates are particularly useful when, for example, it is desired to run several protein-encoding nucleic acid sequences through the same program of sequential mutagenesis.

(2) "Stop" Primers. Specialized primers may also be introduced within the reaction mixture which serve to stop the elongation of products by either failing to be ligated to immediately 5' products, or by binding to a target sequence but failing to prime polymerization in the 3' direction. Such primers are easily constructed by altering their 5' ends to prevent their ligation by a ligase, or altering their 3' ends to prevent their extension by a polymerase. Such stop primers have utility in controlling mutagenized product lengths.

(3) Products as Primers. As will be obvious to those of skill in the art, sequences which serve as primers in one round of mutagenesis serve as templates in subsequent rounds. The converse, however, may also be true: Mutagenic products of one round may serve as primers in one or more subsequent rounds. Thus, for example, mutagenic primers may be designed to produce relatively short (e.g., 10–100 nucleotide) mutagenic products (using, for example, a standard mutagenic primer and a downstream stop primer) which may then serve as primers in subsequent rounds. In the language of computer science, this is equivalent to the program (template) producing new rules (primers) which then operate on the program.

(4) Multiple Primers Per Target. As another level of complexity, as well as an element of non-determinism or stochasticity, multiple mutagenic primers may be employed which, under the reaction conditions, are each capable of binding to a single target sequence. This results in the production of two or more different mutagenic products corresponding to the incorporation of one or the other primer. Indeed, more than two primers may be directed to a single target, and this approach may be applied simultaneously to different targets within the same template, or sequentially to different targets in different rounds. As discussed below, this approach is particularly useful in generating a complex product mixture bearing many differently mutated species.

(5) Limiting Primers. In another variation of the present methods, a stoichiometrically limiting amount of a given primer (mutagenic or outer) may be introduced into the reaction mixture such that, when the primer is consumed (i.e., incorporated into reaction products), one or more reaction products cease to be produced before the completion of the sequential mutagenesis program. The use of such limiting quantities can be used to reduce the potential complexity of the product mixture (relative to the complexity which would be achieved with "unlimited" quantities) or to prevent a target sequence which will come into being at a later round from being mutated by excess primer intended to mutate a substantially similar target during an earlier round.

Thus, for example, if m moles of a given target sequence are present at some round in a given template, then limiting the number of moles of primers which bind to that target sequence may limit the number of moles of product which can be produced from that primer. If, for example, a single double-stranded template molecule is present with sufficient reagents (including appropriate primers for both strands, nucleotides, polymerase and, optionally, ligase) for N additional rounds of synthesis, a target sequence included within that template may increase to approximately $2^N$m moles after N rounds (ignoring any mutagenesis of the target). If, however, a primer which binds to that target is present at less than $2^N$m moles before the N rounds of synthesis, it will be "limiting" and its products will be present at less than $2^N$m moles after the N rounds. More generally, a "limiting primer" is one which is initially present in the reaction mixture at a quantity or stoichiometric ratio such that substantially all copies of the primer will be incorporated into reaction products before the program of sequential mutagenesis has ended. Thus, at any given point in a program of sequential mutagenesis, the quantity of a primer which is "limiting" is a function of the number of moles of target sequence which will subsequently be available during the program (i.e., it is stoichiometric, not absolute), and the number and nature of the subsequent rounds of the program (i.e., it is program dependent).

In one embodiment of this variation, limiting amounts of primers for one ("outer") end of a template may be employed such that the "ends" of the resultant products decrease or "walk" inward, and the portion of the original template available for mutation decreases or "walks" inward. That is, a sufficient amount (stoichiometrically) of a first outer primer (which may or may not be mutagenic as well) may be present to prime synthesis for only N rounds, but a second outer primer, which is "inner" relative to the first, may be present at a higher molar ratio such that it continues to prime synthesis after round N. Alternatively, a second outer primer, still "inner" relative to the first, may become effective after some number of rounds have passed and its target sequence has been created, such that it may continue or begin to prime synthesis after round N. In such cases, early products will differ from later products in their starting position relative to the original template sequence, with later products beginning from a different, more "inner" position.

In another variation, after a limiting primer is exhausted, the products which it produced may be effectively eliminated from the product profile by dilution with the products of subsequent rounds. Because of the inherently exponential nature of nucleic acid polymerization reactions, this dilution may occur quite rapidly. As a result, over many rounds, the reaction product profile may change not only because of the creation of new products, but also because of the extreme dilution of the mutagenized products of limiting primers.

Finally, because the products of limiting primers may be effectively eliminated by dilution, some primers may be effective in hybridizing and priming products for some number of rounds when their target sequences are stoichiometrically abundant, become relatively ineffective for some number of rounds when, due to dilution, their target sequences become relatively rare stoichiometrically, and then become effective again when a subsequent round of the sequential mutagenesis program again creates their target sequences in relatively abundant amounts.

(6) Protein Elements. A variety of proteins may also be added to the reaction mixtures of the present invention in order to influence the mutagenic product profiles. For example, single stranded and double stranded DNA or RNA binding proteins (e.g., recA, Gal4, LexA) may be used to influence the binding of primers to particular targets, to influence the ability of primers to be extended by polymerase, or to influence the ability of primers and/or newly synthesized nucleic acids to be ligated into longer products. Obviously, such proteins with sequence-specific binding may have the greatest utility. In addition, restriction endonucleases are particularly contemplated as being useful proteins in the present invention. Such enzymes may, for example, be present in the reaction mixture but initially lack a sequence-specific substrate until one is provided by a round of mutagenesis which produces a mutagenic product with the appropriate restriction site.

E. Product Mixtures

It should be noted that the reaction mixtures of the present invention will at all times contain a variety of nucleic acid (or nucleic acid analogs) for a variety of reasons. Therefore, references herein to the mutagenic product of a particular round refer to the major new product or products of that round irrespective of the presence of various other templates, primers and products. Several sources of the complexity of the reaction mixtures are discussed briefly below:

(a) Molecular "Errors." As is well known in the art, the processes of nucleic acid hybridization, polymerase-mediated template-dependent nucleic acid polymerization, and nucleic acid ligation are all subject to "errors" that result from the non-deterministic nature of these chemical processes. Thus, apart from the oligonucleotide-mediated mutagenesis programmed in the present invention, additional random mutations, resulting from incorrect pairing of primers and templates, incorrect incorporation of nucleotides into newly synthesized nucleic acid strands, incorrect ligation of nucleic acids, strand displacement, partial product formation, dimerization of primers, and other known phenomena will result in additional products in the reaction mixture apart from those expected to result from the programmed sequential mutagenesis of the invention. These additional products will create a background of "noise" molecules which, for purposes of exposition, have been ignored until this point. As a general matter, these extraneous molecules can also be ignored in practice. If, however, the level of this "noise" begins to substantially interfere with the production of the desired mutagenic products, standard measures of separation may be employed to reduce the interference by reducing the number of such molecules in the reaction mixture (for example, size separation chromatography or electrophoresis followed by a reconstitution of the reaction mixture at the desired round).

(b) Accumulation of Prior Round Products/Templates. The molecular reactions which characterize oligonucleotide-mediated site-directed mutagenesis do not destroy the templates which are used in each round. In addition, the mutagenic products of each round may serve as templates in the next. Thus, if one begins with a single copy of a single-stranded original template, after N rounds there would be N copies of the first mutagenic product. On the other hand, starting with a single copy of the original template, after N rounds there would be only 1 copy of the Nth round mutagenic product, and intermediate numbers of copies of the intermediate round products. Of course, other limiting factors, such as the availability of free copies of the mutagenic primers, will also affect the product profile. Nonetheless, it should be recognized that the product profile in the reaction mixture may become very complex after a relatively small number of rounds. If, however, the program has an end point after N rounds, at which point no additional or new mutagenic steps are programmed by mutagenic primers (see, e.g., the program of FIG. 4, which ends at ABCSDS), cycling the reaction mixture more than N times will cause more and more of the products to reach the end state. Therefore, for programs which have a termination point, cycling more than the necessary number of rounds will increase the amount of later round products in the reaction mixture.

(c) Multiple Primers Per Target. As noted above, more than one mutagenic primer may be introduced for any particular target sequence. Therefore, a single template may yield more than one mutagenic product. Assuming, for example, that two mutagenic primers have essentially identical concentrations and dissociation constants with a target sequence (and essentially identical efficiencies of 3' extension by polymerase and 5' ligation by ligase), approximately half of the mutagenic products from that template should contain each of the two mutagenic primers. Thus, the number of species in the reaction mixture will be increased. In subsequent rounds, the descendants of these two products may continue to differ, may themselves bifurcate, or may converge. Indeed, as discussed below, the use of mutagenic primers which compete for binding to target sequences introduces a non-deterministic element in the product profiles which has use in certain computational applications and can be used to rapidly generate a greater variety of products for certain applications for generating epitopes or combinatorial protein/peptide libraries.

(d) Error resistance. Many of the ideas of traditional error correcting codes can be applied to symbol encoding in programmed mutagenesis. If all symbol sequences employed differ by at least three base changes, then any single base error will result in a sequence that is closest to its proper base sequence. Mutagenic primers can be designed to anneal to sequences that are one base different than their expected targets to implement a measure of error correction. Thus, it is possible to design sequences and primers that are error resistant, and that can correct single or even multiple-base errors. The trade-off made is an increase in symbol length for a more reliable mutational process.

(e) Lengthening and shortening of mutagenized products. The length of a mutagenized product can differ from the length of its template by the use of mutagenic primers that cause DNA "loop-outs." Such primers match the template at their ends, and if sufficient homology is present in the ends, can permit more bases than are present in the template to be inserted in the mutagenized product. The extra bases are encoded in between the ends of the mutagenic primer. Similarly, the primers can cause the template DNA to loop out, resulting in a mutagenized product that is shorter than the template. It will be obvious to one skilled in the art that these types of mutational events can be combined in arbitrary ways on different cycles to permit the length of mutagenized products to vary on a cycle by cycle basis.

F. Applications

The methods of programmed sequential mutagenesis disclosed herein have numerous applications which will be readily apparent to those of skill in the art. These applications include, but are not limited to, the following:

(1) Combinatorial Mutagenesis. A variety of techniques are now employed in molecular biology to generate variants of protein or peptide sequences. These variants may be useful in generating epitopes for antibody formation, in mutating a protein to identify variants with desired features, or in creating libraries of peptides which may be screened for useful activities. The present invention provides a rapid and effective means of generating such variants by using programmed sequential mutagenesis. The primers of the present invention may, for example, be chosen so as to bind to and mutagenize particular coding sequences wherever they occur. In addition, as discussed above, multiple primers per target may be employed to rapidly expand the populations of templates which are subject to mutagenesis in the subsequent rounds. In addition, because the primers of the present invention can create mutagenized sites in a programmed way, it is possible to make the mutagenic process non-deterministic without being entirely random, thus encouraging or discouraging the production of certain classes of products.

(2) Computational Mutagenesis. Recent research has suggested that it may be possible to perform computation with nucleic acid molecules. The idea underlying computing with nucleic acids is elegant. A problem is encoded in the base sequence of polynucleotide molecules, and the molecules are manipulated to produce final molecules that encode the solution to the problem. The solution is then read by sequencing these molecules. This approach affords a potentially revolutionary way to store and process information because the methodology is able to represent problem solutions as a single molecule, and can perform in a single step computational operations on billions of molecules in solution. Work by Adelman (1994, 1995) has shown that nucleic acids and their reactions can be used to generate, in parallel, enormous numbers of possible combinatorial solutions to mathematical problems which can be expressed as Hamiltonian-path problems. The present invention demonstrates another potential application of molecular genetic reactions to the computational sciences: mutagenic primers may be used to implement "string re-writing" or "re-write on copy," a well known element of programming essential to the development of the computer sciences. Thus, the templates of the present invention may be regarded as "strings" which are re-written by the mutagenic primers of the invention. Alternatively, the primers may be regarded as the "rules" of a computational machine in which the template serves as the "program." The use of the methods of the present invention in nucleic acid-based computational machines is, therefore, another particularly contemplated utility.

G. Selection of Primers and Templates

The general design or selection of primers for oligonucleotide-mediated site-directed mutagenesis is well known in the art and need not be elaborated upon here. For general discussions, see, for example, Chapter 15 of Sambrook et al. (1989) *Molecular Cloning: A Laboratory Manual,* 2nd Edition, Cold Spring Harbor Laboratory Press, Cold Spring Harbor, N.Y., or Piechocki and Hines (1994) *BioTechniques* 16(4): 702–707). In the context of the present invention, however, several points are worth noting. (1) The placement of mismatches in the mutagenic primers of the present invention may be controlled so as to prevent or promote certain reactions. Thus, for example, mismatches between a target and a primer at the 5' end of the primer will substantially inhibit ligation of the primer to an adjacent 5' sequence by a ligase, whereas mismatches at the 3' end will substantially inhibit 3' extension of the primer by a polymerase. Where a primer has nearly identical affinity for two different targets, therefore, the choice of mismatches may be used to drive the product profile in a particular direction. (2) When it is desired to use programmed sequential mutagenesis to produce combinatorial mutational variants of proteins or peptides, the templates may be designed so as to employ only a subset of the codons available for each amino acid. This may simplify the design of mutagenic primers and allow certain primers to bind at several sequences encoding a common amino acid sequence. Conversely, codons in particular sequences may be intentionally chosen so as to prevent primer binding and mutagenesis. Thus, not only the primers, but also the templates, may be designed so as to program the mutagenic sequence. (3) For computational applications, the design of the template may be as important and complicated as the design of the primers. Thus, the simple template of FIG. 3 may be regarded as one extreme. Other computational templates may include recurring patterns and nested patterns which will program certain sequences of mutations and/or cause iterations of certain mutagenic patterns. Finally, (4) primers with internal complementarities or which can form intramolecular secondary structures are preferably avoided.

In addition to the fact the that primers of the invention may be nucleic acid analogs (e.g., with modified bases or phosphodiester linkages), the primers may also be labeled in varying ways. Radioactive labels, for example, can be useful in identifying mutagenized products (see FIG. 5). Similarly, biochemical labels such as biotin or other ligands can be useful for the separation or purification of particular mutagenized products from complex product profiles. Consonant with the present teachings, essentially any such labels which do not substantially interfere with the ability of the primers to hybridize to their target sequences and to support polymerase-dependent nucleic acid synthesis may be employed.

H. Programmed Sequential Mutagenesis Reagents

In another aspect, the present invention provides for reagents for use in programmed sequential mutagenesis. These reagents comprise mixtures of mutagenic primers for the above-described methods and, therefore, comprise mixtures of (1) a first set of one or more mutagenic primers which will bind to one or more target sequences within a template sequence under at least one set of conditions permissive for polymerase-mediated nucleic acid synthesis to create a first set of one or more mutagenized products, and (2) a second set of one or more mutagenic primers which will not bind to any target sequence within the original template sequence under those conditions, but which will bind to target sequences in the mutagenized products of the first set of mutagenic primers, under substantially similar conditions permissive for polymerase-mediated nucleic acid synthesis to create a second set of one or more mutagenized products.

As one example of such products and their utility, consider mutagenic reagents for programmed sequential mutagenesis of nucleic acids encoding an amino acid sequence of the form $X_1A_1X_2A_2X_3$, where each $X_i$ is any sequence of between zero and twenty amino acids, and each $A_i$ is one or more independently selected amino acids. Such polypeptides are encoded by nucleic acids of the form $Y_1C_1Y_2C_2Y_3$, where each $Y_i$ is any sequence of between zero and twenty codons, and each $C_i$ is one or more independently selected codons. In light of the foregoing discussion, a first set of mutagenic primers may be selected which will alter these nucleic acid templates to $Y_1M_iY_2C_2Y_3$ or $Y_1C_1Y_2M_iY_3$, where $M_i$ is any codon sequence which alters the encoded amino acid sequence. In particular, the first set of mutagenic primers may include a multiplicity of mutagenic primers which alter the codon sequences such that the mutagenized products encode a multiplicity of related polypeptide sequences (e.g., a set of mutagenized products in which $M_i$ may be each of the other possible amino acids). Next, a second set of mutagenic primers may be selected which win not bind to and mutagenize the original sequence, $Y_1C_1Y_2C_2Y_3$, but which will further mutagenize, in a second programmed round, the sequences $Y_1M_iY_2C_2Y_3$ or $Y_1C_1Y_2M_iY_3$ to produce, respectively, sequences $Y_1M_iY_2M_jY_3$ or $Y_1M_jY_2M_iY_3$, where $M_j$ is any codon sequence which further alters the encoded amino acid sequence. Naturally, the first and second sets of mutagenic primers may be selected to operate on the same or opposite strands, and intervening rounds of nucleic acid synthesis, which do not mutagenize the products, may be employed to amplify all or some products.

Such programmed sequential mutagenesis primers need not operate on peptide-encoding sequences and the term "codon" in the description above may be replaced generically by "target sequence." Nonetheless, such reagents are expected to have particular utility in creating combinatorial diversity in polypeptides by providing a single reagent mixture useful in the methods of the present invention. Such combinatorial diversity in polypeptides is expected to be particularly useful in developing and screening polypeptides for activity as agonists or antagonists of biological receptors, as antigens or anergens, and as polypeptide-based pharmaceuticals generally.

As will be obvious from the foregoing, the programmed sequential mutagenesis reagents may comprise two or more different sets of mutagenic primers for operation on two or more different target sequences in two or more different rounds of programmed sequential mutagenesis. These mutagenic primers also will be subject to the same preferred ranges of length (e.g., at least 10, 15 or 20 nucleotides or nucleotide analogs), and the same preferred numbers of non-complementary bases as was previously described for mutagenic primers. Preferably, a reagent will contain 3–10 different sets of mutagenic primers for operation on 3–10 different target sequences in 3–10 different rounds of mutagenesis. In most preferred embodiments, a set of mutagenic primers for a single target will introduce mutations altering at least one codon to each of two or more, preferably 3–10 or 10–19, different codons. The programmed sequential mutagenesis reagents may be packaged in any convenient form, optionally including outer primers, enzymes and other factors needed for an in vitro reaction mixture.

EXAMPLES

A program of sequential mutagenesis was developed similar to that shown in FIG. 3. First, a double-stranded 132 base pair oligonucleotide sequence was synthesized including a 72 nucleotide original template, $S_{OLIGO}$, with 30 nucleotides of flanking sequence at each end. The $S_{OLIGO}$ sequence included a 12 nucleotide sequence, $S_A$, followed by five repeats of another 12 nucleotide sequence, $S_C$:

$S_{OLIGO}$:
5'-(30)-$S_A S_C S_C S_C S_C S_C$-(30)-3'
3'(30)-$\overline{S}_A \overline{S}_C \overline{S}_C \overline{S}_C \overline{S}_C \overline{S}_C$-(30)-5'

A 115 base pair subsequence, including $S_{OLIGO}$, was PCR amplified using engineered primers that added new EcoRI and BamHI sites to the amplified product on the 5' and 3' ends respectively. The amplified product was digested with both EcoRI and BamHI enzymes. The vector pBluescript-II KS was also digested with both enzymes and de-phosphorylated, and the insert was then ligated into the vector and transformed into competent cells. A clone that contained the insert sequence was identified by sequencing. The clone was used to prepare a stock of double stranded plasmid DNA and the DNA was then restricted with BamHI.

Mutagenic primers were then chosen to perform the following sequential mutations:

Mutagenized Product 1 5'-(30)-$S_A S_B S_C S_C S_C S_C$-(30)-3'
Mutagenized Product 2 3'(30)-$\overline{S}_A \overline{S}_B \overline{S}_A \overline{S}_C \overline{S}_C \overline{S}_C$-(30)-5'
where

| | |
|---|---|
| $S_A$=5'-AAC GGA TTA CGC-3' | (SEQ ID NO: 1) |
| $S_B$=5'-TTC CGA TAA CGC-3' | (SEQ ID NO: 2) |
| $S_C$=5'-TAC CGA TTA CGC-3' | (SEQ ID NO: 3) |

Thus, in the first round, the target sequence is $\overline{S}_A \overline{S}_C$ and the subsequence $S_C$ is mutagenized to $S_B$ by changing an A to a T (at nucleotide position 2 from the 5' end of $S_C$), and a T to an A (at nucleotide position 8 from the 5' end of $S_C$). In the next round, the target sequence is $S_B S_C$ and the subsequence $\overline{S}_C$ is mutagenized to $\overline{S}_A$ by changing an A to a T (at nucleotide position 1 from the 3' end of $\overline{S}_C$), and a G to a C (at nucleotide position 4 from the 3' end of $\overline{S}_C$).

All primers were prepared with four phosphorothioate linkages on their 3' ends to resist degradation by exo+ polymerases. Outer primer 1 was constructed to correspond to the 5' flanking region of the "sense" strand of $S_{OLIGO}$ and, therefore, to bind to the 3' flanking region of the complementary or "antisense" strand. Similarly, Outer Primer 2 was constructed to correspond to the 5' flanking region of the "antisense" strand of $S_{OLIGO}$ and, therefore, to bind to the 3' flanking region of the complementary or "sense" strand. In addition, the two mutagenic primers, $M_{C \to A}$ and $M_{C \to B}$ were constructed:

| | |
|---|---|
| $M_{C \to A}$=5'-GCG TAA TCC GTT GCG TTA TCG GAA-3' | (SEQ ID NO: 4) |
| $M_{C \to B}$=5'-AAC GGA TTA CGC TTC CGA TAA CGC-3' | (SEQ ID NO: 5) |

Note that $M_{C \to A}$ is equivalent to a 5'→3' ligation of $\overline{S}_A$ and $\overline{S}_B$ and that $M_{C \to B}$ is equivalent to 5'→3' a ligation of $S_A$ and $S_B$. Note, however, that $M_{C \to A}$ (5'-$\overline{S}_A \overline{S}_B$-3') is not the complement of $M_{C \to B}$ (5'-$S_A S_B$-3') because the 5'→3' directionality is not reversed.

Six reactions mixtures, designated R-1 through R-6, were prepared, each of which contained:

2 pM Outer Primer 1
2 pM Outer Primer 2
0.2 pM phosphorylated $M_{C \to A}$ oligo
0.2 pM phosphorylated $M_{C \to B}$ oligo
0.5 pM $S_{OLIGO}$ double stranded DNA (BamHI restricted)
1 µl 10× Vent-NAD+ buffer in a total volume of 7.5 microliters. 10× Vent-NAD+ buffer was created by adding 10 mM NAD+ to 10× Vent buffer (New England BioLabs). Two negative control reactions were also prepared, one that did not include the $M_{C \to A}$ oligo, and one that did not include the $M_{C \to B}$ oligo. The reactions were overlaid with mineral oil, and placed in a thermal cycler that was programmed for a cycle of 10 minutes at 94° C., followed by a repetitive cycle that was 30 minutes at 50° and 2 minutes at 94°. During the first 94° cycle 0.5 µl of 0.5 U/µl Vent exo+(New England BioLabs) and 1 µl of 40 U/µl of Taq Ligase (New England BioLabs) was added to each well.

Before the end of the first 94° cycle 1 µl of 0.2 µM $^{32}$P γ-end-labeled $M_{C \to B}$ was added to R-1, and 1 µl of 0.2 µM $^{32}$P-$M_{C \to A}$ was added to R-2. At the end of the first 30 minute 50° cycle, sequencing stop-loading dye was added to R-1 and R-2 and they were removed from the thermal cycler. In a similar fashion, $^{32}$P-$M_{C \to A}$ and $^{32}$P-$M_{C \to B}$ were added to R-3 and R-4 during the second denaturing cycle and before the second 50° cycle and then stopped at the end of the second 50° cycle, and $^{32}$P-$M_{C \to A}$ and $^{32}$P-$M_{\to B}$ were added to R-5 and R-6 respectively in the third cycle. During the tenth 94° cycle $^{32}$P-$M_{C \to B}$ was added to the negative control without $M_{C \to A}$, and $^{32}$P-$M_{C \to A}$ was added to the negative control without $M_{C \to B}$, and both negative control reactions were stopped at the end of the tenth 30 minute 50° cycle.

Figure 5:
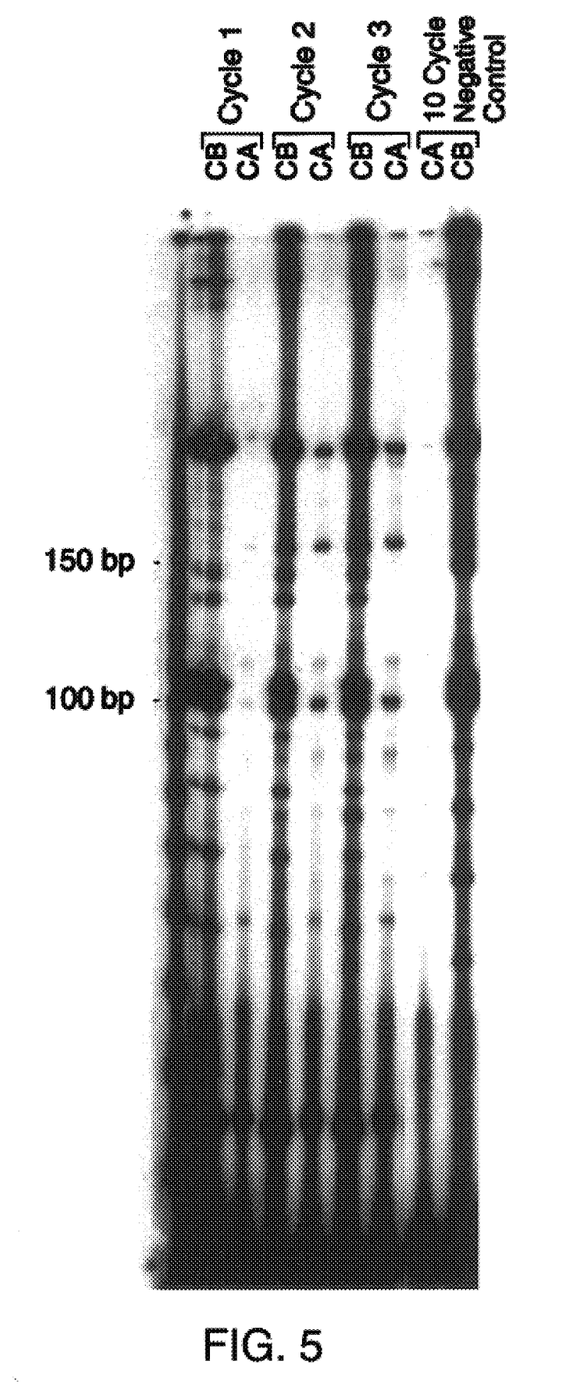
FIG. 5. This figure is a photograph of an electrophoretic gel showing product profiles arising from programmed sequential mutagenesis.

After the reactions were stopped, all samples were heated at least five minutes at 85° C. and then 3 µl was analyzed on a 6% denaturing acrylamide gel. A representative electrophoretic gel is shown in FIG. 5, which is described below.

Cycle 1, CB lane. The CB lane shows an autoradiograph of product labeled with 32P-$M_{C \to B}$. In cycle 1 the reaction system completes the first programmed round of mutagenesis, or counts "one." The band at approximately 228 bp is a full length first mutagenized product that represents a successful ligation of the upstream Outer Primer 1 product to the $M_{C \to B}$ product that is generated by binding to and polymerization from the Outer Primer 1 and $\overline{S}_A \overline{S}_C$ target sequences, followed by ligation of these two products (FIG. 3a). R-1 and R-2 also show bands at 102/107 base pairs that are a result of $M_{C \to B}$ binding to and polymerization from the $\overline{S}_A \overline{S}_C$ target sequence but without successful ligation to the Outer Primer 1 product. The 102 band is from product that has been generated from an original template generated by Outer Primer 2, while the 107 band is from the original plasmid DNA that is five bases longer because of the overhanging BamHI site.

Cycle 1, CA lane. The CA lane shows an autoradiograph of product labeled with $^{32}$P-$M_{C \to A}$. A small amount of various products are seen that correspond to second round products because, as noted above, the system can undergo multiple rounds of mutagenesis per thermal cycle. Thus, these products include a 102 bp product (Outer Primer 2 product ligation to $M_{C \to A}$ product, using a failed first round product as a template), a 159 bp product ($M_{C \to A}$ extension on a full length first round product with a failed Outer Primer 2 ligation), and a 225 bp product (successful $M_{C \to A}$ extension and Outer Primer 2 product ligation). In the absence of $M_{C \to B}$, no detectable product is present in the $M_{C \to A}$ lane in cycle 1 even with overexposure (data not shown).

Cycle 2. In cycle 2 the CB lane shows more first cycle product, and the CA lane shows that the system has clearly entered the second round of the program, or counted to "two."

Cycle 10. The negative control without $M_{C \to A}$ (lane CB) shows a very large amount of product from the first round of mutagenesis. The negative control without $M_{C \to B}$ (lane CA) shows that the $M_{C \to B}$ mutagenesis step is necessary (i.e., a condition precedent) to perform the second round of mutagenesis, as it only has a barely detectable amount of second round products, even after 10 cycles.

References

Adelman (1994), Science 266: 1021–1024.

Adelman (1995), "On Constructing a Molecular Computer," Draft Report, Department of Computer Science, UCLA Baum (1995), Science 268:583–585.

Breslauer et al. (1986), Proc. Natl. Acad. Sci. (USA) 83:3746–3750.

Garcy et al. (1979), Computers and Intractability: A Guide to the Theory of NP-Completeness, W. H. Freeman.

Gifford (1994), Science 266: 993–994.

Head (1987), Bul. Math. Biology 49: 737–759.

Hutchison and Edgell (1971), J. Virol. 8:181.

Lipton (1995) Science 268:542–545.

Piechocki and Hines (1994), BioTechniques 16(4): 702–707.

Sambrook et al. (1989), Molecular Cloning: A Laboratory Manual, 2nd Edition, Cold Spring Harbor Laboratory Press, Cold Spring Harbor, N.Y.

Werntges et al. (1986), Nucleic Acids Res. 14:3773–3790.

What is claimed is:

1. A method for performing programmed sequential mutagenesis of nucleic acids comprising providing an original template nucleic acid or nucleic acid analog including a first target sequence;

providing a first mutagenic primer nucleic acid or nucleic acid analog including a first target-binding sequence capable of hybridizing to said first target sequence under conditions permissive for polymerase mediated nucleic acid synthesis, but which is non-complementary to said first target sequence at one or more nucleotide or nucleotide analog positions;

subjecting said original template and said first mutagenic primer to a first round of nucleic acid synthesis to produce a first mutagenized nucleic acid or nucleic acid analog including a second target sequence which is neither identical nor complementary to any sequence in said original template nucleic acid or nucleic acid analog;

providing a second mutagenic primer nucleic acid or nucleic acid analog including a second target-binding sequence capable of hybridizing to said second target sequence under conditions permissive for polymerase mediated nucleic acid synthesis, but which is non-complementary to said second target sequence atone or more nucleotide or nucleotide analog positions; and subjecting said first mutagenized nucleic acid or nucleic acid analog and said second mutagenic primer to a second round of nucleic acid synthesis to produce a second mutagenized nucleic acid or nucleic acid analog including a third target sequence which is neither identical nor complementary to any sequence in said original template or first mutagenized nucleic acid or nucleic acid analogs.

2. A method as in claim 1 wherein said first mutagenic primer and said second mutagenic primer are present in a single reaction mixture during said first round of nucleic acid synthesis, and wherein said second mutagenic primer is substantially incapable of binding to said original template nucleic acid under said conditions of said first round.

3. A method as in claim 1 wherein said method further comprises providing at least a third mutagenic primer having a target sequence not present in said original template nucleic acid, and subjecting said nucleic acids or nucleic acid analogs to additional rounds of nucleic acid synthesis.

4. A method as in any one of claims 1–3 wherein said rounds of nucleic acid synthesis comprise DNA polymerase-mediated nucleic acid synthesis in vitro.

5. A method as in claim 4 wherein said nucleic acid synthesis in vitro is part of a thermally cycled polymerization reaction.

6. A method as in any one of claims 1–3 further comprising providing a first outer primer including a sequence capable of hybridizing to said template nucleic acid at a site 3' of said first target sequence under conditions permissive for polymerase mediated nucleic acid synthesis.

7. A method as in any one of claims 1–3 further comprising providing a second outer primer including a sequence capable of hybridizing to said first mutagenized nucleic acid at a site 3' of said second target sequence under conditions permissive for polymerase mediated nucleic acid synthesis.

8. A method as in any one of claims 1–3 wherein said target sequences comprise a sequence of at least 10 nucleotides or nucleotide analogs.

9. A method as in any one of claims 1–3 wherein said target sequences comprise a sequence of at least 15 nucleotides or nucleotide analogs.

10. A method as in any one of claims 1–3 wherein said target sequences comprise a sequence of at least 20 nucleotides or nucleotide analogs.

11. A method as in claim 8 wherein said mutagenic primers comprise a sequence of at least 10 nucleotides or nucleotide analogs; and wherein said target-binding sequences are non-complementary to their target sequences at 1–4 nucleotides or nucleotide analog positions.

12. A method as in claim 9 wherein said mutagenic primers comprise a sequence of at least 15 nucleotides or nucleotide analogs; and wherein said target-binding sequences are non-complementary to their target sequences at 1–7 nucleotides or nucleotide analog positions.

13. A programmed sequential mutagenesis reagent comprising a first set of one or more mutagenic primers which will bind to one or more target sequences within a template sequence under first conditions permissive for polymerase-mediated nucleic acid synthesis to create a first set of one or more mutagenized products; and a second set of one or more mutagenic primers which will not bind to any target sequence within said template sequence under said first conditions, but which will bind to one or more target sequences in said first set of mutagenized products under conditions permissive for polymerase-mediated nucleic acid synthesis to create a second set of one or more mutagenized products.

* * * * *